(12) United States Patent
Brocard-Masson et al.

(10) Patent No.: US 9,994,888 B2
(45) Date of Patent: Jun. 12, 2018

(54) PROCESS FOR PREPARING GENETICALLY TRANSFORMED YEASTS CAPABLE OF PRODUCING A MOLECULE OF INTEREST AT A HIGH TITRE

(75) Inventors: Corinne Brocard-Masson, Paris (FR); Isabelle Bonnin, Paris (FR); Bruno Dumas, Paris (FR)

(73) Assignee: SANOFI, Paris (FR)

( * ) Notice: Subject to any disclaimer, the term of this patent is extended or adjusted under 35 U.S.C. 154(b) by 363 days.

(21) Appl. No.: 14/127,396

(22) PCT Filed: Jun. 18, 2012

(86) PCT No.: PCT/EP2012/061601
§ 371 (c)(1),
(2), (4) Date: Dec. 18, 2013

(87) PCT Pub. No.: WO2012/175453
PCT Pub. Date: Dec. 27, 2012

(65) Prior Publication Data
US 2014/0186885 A1 Jul. 3, 2014

(30) Foreign Application Priority Data
Jun. 21, 2011 (FR) ...................................... 11 55462

(51) Int. Cl.
*C12P 33/00* (2006.01)
*C12N 15/81* (2006.01)
(Continued)

(52) U.S. Cl.
CPC .............. *C12P 33/00* (2013.01); *C07K 14/79* (2013.01); *C12N 9/0006* (2013.01);
(Continued)

(58) Field of Classification Search
None
See application file for complete search history.

(56) References Cited

U.S. PATENT DOCUMENTS 5,939,318 A * 8/1999 Miller .................. C12N 9/0081
435/183
6,136,576 A * 10/2000 Diaz-Torres ......... C12N 9/0004
435/158

(Continued)

FOREIGN PATENT DOCUMENTS

FR  2820145 A1   8/2002

OTHER PUBLICATIONS

Old et al., "Principles of Gene Manipulation. An Introduction to Genetic Engineering", Studies in Microbiology, vol. 2, Fourth Edition, Blackwell Scientific Publications, Oxford, pp. 199-221 (1989).*

(Continued)

*Primary Examiner* — Robert B Mondesi
*Assistant Examiner* — Richard C Ekstrom
(74) *Attorney, Agent, or Firm* — Lathrop Gage LLP; James H. Velema, Esq.

(57) ABSTRACT

The subject of the present invention is a process for preparing a genetically modified yeast by multicopy integration of at least four expression cassettes, allowing the production of a molecule of interest at high titer. The subject of the present invention is also yeasts transformed according to said process, and the use thereof for producing hydrocortisone.

12 Claims, 5 Drawing Sheets

(51) Int. Cl.
*C12N 9/04* (2006.01)
*C07K 14/79* (2006.01)
*C12N 9/02* (2006.01)

(52) U.S. Cl.
CPC ......... *C12N 9/0079* (2013.01); *C12N 9/0081* (2013.01); *C12N 15/81* (2013.01); *C12Y 101/01051* (2013.01)

(56) References Cited

U.S. PATENT DOCUMENTS

| 2002/0197704 | A1* | 12/2002 | Gellissen | C12N 9/90 435/232 |
| 2004/0082025 | A1* | 4/2004 | Dumas | C12N 9/0087 435/52 |
| 2004/0137556 | A1* | 7/2004 | Spagnoli | C12P 33/005 435/60 |
| 2006/0269986 | A1* | 11/2006 | Kunkel | C12P 33/00 435/61 |
| 2009/0239837 | A1* | 9/2009 | Pompon | A61K 51/0493 514/182 |

OTHER PUBLICATIONS

International Search Report for International Application No. PCT/EP2012/061601, dated Sep. 4, 2012, 5 pages.

Nevoigt et al. 'Progress in metabolic engineering of *Saccharomyces cerevisiae*'. Microbiology and Molecular Biology Reviews. 2008, vol. 72, No. 3, pp. 379-412.

Mendoza-Vega et al. 'Industrial production of heterologous proteins by fed-batch cultures of the yeast *Saccharomyces cereuisiae*'. FEMS Microbiology Reviews. 1994, vol. 15, No. 4, pp. 369-410.

Fang et al. 'A vector set for systematic metabolic engineering in *Saccharomyces cerevisiae*'. Yeast. 2011, vol. 28, No. 2, pp. 123-136.

International Preliminary Report on Patentability for International Application No. PCT/EP2012/061601, dated Dec. 23, 2013, 7 pages.

* cited by examiner

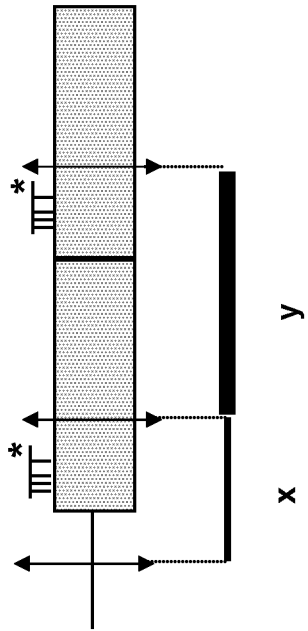
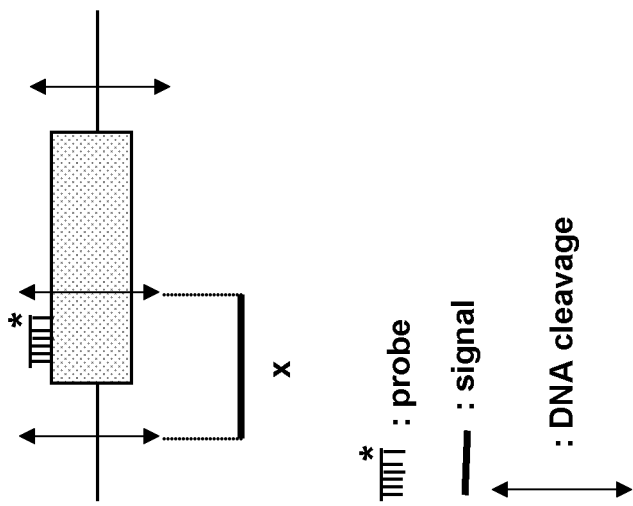
Figure 5 A
Figure 5 B

SEQUENCE LISTING

```
<160> NUMBER OF SEQ ID NOS: 8

<210> SEQ ID NO 1
<211> LENGTH: 327
<212> TYPE: DNA
<213> ORGANISM: Artificial
<220> FEATURE:
<223> OTHER INFORMATION: R1

<400> SEQUENCE: 1
atggcccttc aagctgcttt ctttggtctc ctctgctttc tctgtccgca aagatggaaa      60
attaaatgct tcagcatcat catcattcaa agagtctagt ctgttcggtg tttcactttc     120
ggagcaaagc aaagctgact ttgtctcttc ctcattgaga tgcaagaggg aacagagctt     180
gaggaataat aaagcgatta ttcgagctca agcaatcgcg acttcaactc catcagtcac     240
aaaatcttcc ttagaccgca agaaaacact tagaaaagga aacgtggttg tcacgggagc     300
ttcttcaggg ctaggtttag caacggc                                         327

<210> SEQ ID NO 2
<211> LENGTH: 336
<212> TYPE: DNA
<213> ORGANISM: Artificial
<220> FEATURE:
<223> OTHER INFORMATION: R2

<400> SEQUENCE: 2
ataatggcgt gcagagactt cctcaaggct gagagagccg ctcaatctgc agggatgcct      60
aaggacagct acactatgat gcatttggac ttggcgtctt tggacagcgt gaggcagttt     120
gttgataact tcaggcgagc tgagatgcct ctcgatgtgt tggtctgcaa tgccgcagtc     180
tatcagccaa cggctaatca acctactttc actgctgaag ggtttgagct tagcgttggg     240
ataaaccatt tgggccactt tcttctttca agattgttga ttgatgactt gaagaactcc     300
gattatccat caaaacgtct catcattgtt ggtacc                               336

<210> SEQ ID NO 3
```

```
<211> LENGTH: 20
<212> TYPE: DNA
<213> ORGANISM: Artificial
<220> FEATURE:
<223> OTHER INFORMATION: 3betaHSD-F

<400> SEQUENCE: 3
gacgggatgg cagggtggag                                                   20

<210> SEQ ID NO 4
<211> LENGTH: 20
<212> TYPE: DNA
<213> ORGANISM: Artificial
<220> FEATURE:
<223> OTHER INFORMATION: 3betaHSD-R

<400> SEQUENCE: 4
agtgaatctt tgttttcagg                                                   20

<210> SEQ ID NO 5
<211> LENGTH: 20
<212> TYPE: DNA
<213> ORGANISM: Artificial
<220> FEATURE:
<223> OTHER INFORMATION: P450scc-F

<400> SEQUENCE: 5
ctcccctggt gacaatggct                                                   20

<210> SEQ ID NO 6
<211> LENGTH: 20
<212> TYPE: DNA
<213> ORGANISM: Artificial
<220> FEATURE:
<223> OTHER INFORMATION: P450scc-R

<400> SEQUENCE: 6
ggttgggtca aacttgtccg                                                   20

<210> SEQ ID NO 7
<211> LENGTH: 1156
<212> TYPE: DNA
<213> ORGANISM: Artificial
<220> FEATURE:
<223> OTHER INFORMATION: P450scc PROBE

<400> SEQUENCE: 7
ctcccctggt gacaatggct ggcttaacct ctaccatttc tggagggaga agggctcaca       60
gagaatccac tttcgccaca tcgagaactt ccagaagtat ggccccattt acagggagaa      120
gcttggcaat ttggagtcag tttatatcat tcaccctgaa gacgtggccc atctcttcaa      180
gttcgaggga tcctacccag agagatatga catcccgccc tggctggcct atcaccgata      240
ttatcagaaa cccattggag tcctgtttaa gaagtcagga acctggaaga agaccgggt      300 ggtcctgaac acggaggtga tggctccaga ggcaataaag aacttcatcc cactgctgaa      360
tccagtgtct caggacttcg tcagcctcct gcacaagcgc atcaagcagc agggctccgg      420
aaagtttgta ggggacatca aggaagacct gtttcacttt gcctttgagt ccatcaccaa      480
tgtcatgttt ggggagcgcc tggggatgct ggaggagaca gtgaaccccg aggcccagaa      540
gttcattgat gccgtctaca agatgttcca caccagtgtc cctctgctca acgtccctcc      600
agaactgtac cgtctattca gaaccaagac ttgagggac catgtagccg catgggacac      660
aattttcaat aaagctgaaa aatacactga gatcttctac caggacctga gacggaaaac      720
```

-continued

```
agaatttagg aattacccag gcatcctcta ctgcctcctg aaaagtgaga agatgctctt        780
ggaggatgtc aaggccaata ttacggagat gctggcaggg ggtgtgaaca cgacatccat        840
gacattgcaa tggcacttgt acgagatggc acgcagcctg aatgtgcagg agatgctgcg        900
ggaggaggtt ctgaatgccc gacgccaggc agagggagac ataagcaaga tgctgcaaat        960
ggtcccactt ctcaaagcta gcatcaagga gacgctgaga ctccaccca tctccgtgac        1020 cctgcagaga tacccctgaaa gtgacttggt tcttcaagat tacctgattc ctgccaagac      1080
actggtgcaa gtggccatct atgccatggg ccgagaccct gccttcttct ccagtccgga       1140
caagtttgac ccaacc                                                       1156

<210> SEQ ID NO 8
<211> LENGTH: 1126
<212> TYPE: DNA
<213> ORGANISM: Artificial
<220> FEATURE:
<223> OTHER INFORMATION: 3betaHSD probe

<400> SEQUENCE: 8
gacgggatgg cagggtggag ctgcctcgtg accggaggag gaggctttct gggccagagg        60
atcatctgcc tgttggtgga ggagaaggat ctgcaggaaa tccgggtgct agacaaagtc       120
ttcagaccag aagttcggga ggaattttct aagctccaga gcaagatcaa gctgaccctg       180
ctggaaggag acattctgga tgagcagtgc ctgaaggggg cctgccaggg cacctcagtg       240
gtcatccaca ccgcctctgt cattgacgtc aggaatgctg tcccgcgaga gaccatcatg       300
aacgtcaatg tgaaaggtac ccagctgctg ttggaggcct gtgtccaggc cagcgtaccg       360 gtcttatcc acaccagcac catagaagtg gctgggccca actcctacag ggagatcatc       420
caagacggcc gtgaagaaga gcatcatgaa tcggcatggt cctctccata cccatacagc       480
aagaagcttg ccgagaaggc tgtgctggga gctaatgggt gggctctgaa aaatggtggc       540
accttgtaca cttgtgccct gaggcccatg tacatctacg gggaggggag cccattcctt       600
tctgcctaca tgcacggagc cttgaataac aacggcatcc tgaccaatca ctgcaagttc       660
tcaagagtca acccagtcta tgttggcaat gtggcctggg cccacattct ggccttgagg       720
gccctgaggg accccaaaaa ggtcccaaac atccaaggac agttctacta catctcagac       780
gacacgccac accaaagcta cgatgacctc aattacactt tgagcaaaga atggggcttc       840
tgcctggatt cccggatgag ccttcctatt tctctgcagt actggcttgc cttcctgctg       900
gaaatagtga gcttcctgct cagtccaatt tacaaatata acccttgctt caaccgccac       960
ctagtgactc tttccaacag cgtgttcacc ttctcctata agaaagctca gcgagatctg      1020
gggtatgagc ccctctacac ttgggaggaa gccaagcaga aaaccaagga gtggattggc      1080
tccctggtga aacagcacaa agagaccctg aaaacaaaga ttcact                     1126
```

PROCESS FOR PREPARING GENETICALLY TRANSFORMED YEASTS CAPABLE OF PRODUCING A MOLECULE OF INTEREST AT A HIGH TITRE

RELATED APPLICATIONS

This application is a 35 U.S.C. § 371 filing of International Application No. PCT/EP2012/061601, filed Jun. 18, 2012; which claims priority to French Patent Application No. 1155462, filed on Jun. 21, 2011. The entire contents of each are incorporated herein by reference.

The subject of the present invention is a process for preparing a genetically modified yeast by multicopy integration of at least four expression cassettes, allowing the production of a molecule of interest at high titre. The subject of the present invention is also yeasts transformed according to said method, and the use thereof for producing hydrocortisone.

Recombinant Protein Production

The baker's yeast *Saccharomyces cerevisiae* was selected as a host organism for producing recombinant proteins because of its eukaryotic cell characteristics related to those of mammals, including post-translational modifications of the proteins synthesized, such as acetylation, phosphorylation and glycosylation, but also because of the ease with which it can be genetically manipulated, the availability of its genomic sequence, the control of large-scale fermentation processes for microorganisms of this type and the lack of danger to humans, animals or plants (classified GRAS, Generally Recognized As Safe). These characteristics have made it an organism of choice widely used in the food-processing industry and more recently in the pharmaceutical field.

*Saccharomyces cerevisiae* can be used to produce compounds of varied industrial uses by virtue of its ability to synthesize various metabolites in the natural state, such as enzymes, organic acids, polysaccharides or organoleptic compounds. In particular, a variety of endogenous fatty acids and sterols can be used to produce cosmetological or pharmaceutical agents such as provitamin D2 produced from ergosterol. Endogenous sterol compounds are also precursors of heterologous molecules that can be obtained after genetic engineering of *Saccharomyces cerevisiae* strains. Examples include taxadien-5-acetoxy-10-ol, a precursor of taxol, artemisinic acid, a compound that is part of the composition of an antimalarial agent, and steroid hormones.

Hydrocortisone Production in the *Saccharomyces cerevisiae* Yeast

Hydrocortisone remains, more than fifty years after it was first placed on the market, a therapeutic molecule that is used for its anti-inflammatory properties or as a synthesis intermediate for derived steroid substances.

Steroid production is currently associated with expensive and polluting extraction or synthesis processes comprising a bioconversion step and several chemical synthesis steps. The development of an alternative process, which is less expensive, has been sought.

The development of such a process was initiated in the 1990s. It involves using a genetically modified *Saccharomyces cerevisiae* strain. Proof of the concept was demonstrated in 1999 and subsequently confirmed (WO 02/061109; Ménard Szczebara et al., 2003). The yeast were modified to express several heterologous proteins and to inactivate several endogenous proteins in order to eliminate parasitic reactions. These modified yeast strains are capable of producing, by fermentation from a simple carbonaceous source, hydrocortisone via the mammalian biosynthesis pathway reconstituted in this organism (Brocard-Masson and Dumas, 2006; Dumas B. et al., 2006).

However, these first strains showed a low capacity for producing hydrocortisone and did not therefore meet the requirements of an industrial production.

Yeast Transformation Methods

One strategy to increase strain productivity is to improve the transformation processes for introducing heterologous genes into a yeast cell. Transformation processes are typically accompanied by a selection, according to a suitable method, of the best transformants.

Among the conventional processes for transformation of yeast strains, mention may in particular be made of that proposed by Ito et al. (1983), or by Klebe et al. (1983). In the particular case of transformation with linear DNA fragments, a spheroplast transformation technique such as that proposed by Becker and Lundblad (2001) will be preferentially used.

In order to increase protein expression, one strategy is to introduce several copies of a gene of interest into a yeast strain. Typically, yeast vectors are autonomously replicating plasmids which contain a gene encoding a selectable marker, as well as a 2 μm yeast origin of replication (Broach, 1983). The 2 μm origin allows multiple copies of the plasmid to be present in each cell. Selective pressure is used to maintain the plasmid in the cell (i.e. the cells are cultured in a chemically defined medium such that only cells carrying the plasmid bearing the selective marker can grow).

However, the use of autonomously replicating, high copy vectors is not applicable for certain industrial production processes using complex raw materials. Furthermore, the number of genes that can be cloned on such a plasmid vector is generally limited to two or three expression cassettes, because the size of the plasmid effects the efficiency of transformation and replication.

Another strategy has been described by Lopes et al. (1989 and 1991). It consists of the construction of a multiple integration vector, called pMIRY2 for Multiple Integration into the Ribosomal DNA from Yeast, which targets the ribosomal DNA (rDNA) of the *Saccharomyces cerevisiae* genome. The gene of interest to be expressed, carried by the pMIRY2 plasmid, is inserted into the ribosomal DNA composed of approximately 100 to 200 tandem repeat units located on chromosome XII. It is integrated at the rDNA locus initially at low copy number, and then can be amplified by applying a strong selection pressure (Lopes et al. 1991).

However, the use of integrating multiple copies of a plasmid into ribosomal DNA also has limitations: this method has been described only for the introduction of a single gene of interest accompanied by a selectable marker.

Accordingly, it would be advantageous to combine the benefits of the introduction of multiple copies of a gene via a 2 μm replication plasmid with that of the stable integration of a gene via an integration plasmid, so as to enable efficient coexpression of several proteins.

The inventors have shown that it is possible to obtain yeasts producing high titres of molecules of interest suitable for an industrial-scale production, by stable multicopy integration of at least four expression cassettes for genes of interest. Thus, high level expression of at least four different genes, each of which is present in multiple copies, can be achieved using the present invention.

SUMMARY OF THE INVENTION

The present invention provides a simple and rapid method for obtaining yeasts producing a molecule of interest at high titre after stable multicopy integration of at least four expression cassettes. The multicopy integration allows, after selection of the best transformants, the high-level expression of the transgenes of interest.

Such a method makes it possible to modify a yeast by providing it with various genes of the same metabolic pathway or of different metabolic pathways. Thus modified, the yeast acquires the ability to convert endogenous molecules or exogenous substrates into a product of interest. Such a transformed yeast can therefore be used as a custom-made biological tool for producing molecules of interest, including recombinant proteins.

One particular subject according to the invention is a yeast expressing 3β-hydroxysteroid dehydrogenase (3β-HSD), steroid 11β-hydroxylase, also called P450c11 (CYP11B1), cytochrome P450 side-chain cleavage (or P450scc) (CYP11A1) and adrenodoxin (ADX), obtained by applying the process according to the invention. A yeast expressing sterol Δ7-reductase, steroid 17α-hydroxylase (CYP17A1), and steroid 21-hydroxylase (CYP21A1), in addition to the four genes mentioned above, can be used to convert endogenous sterols into hydrocortisone.

DETAILED DESCRIPTION OF THE INVENTION

The subject of the present invention is a process for preparing genetically transformed yeasts producing a high titre of molecules of interest, which consists of (i) stable multicopy integration of at least four expression cassettes, followed by (ii) selection of the yeasts which are the best producers.

The step of stable multicopy integration of at least 4 expression cassettes according to the invention is based on the cotransformation of two integration plasmids each comprising at least two expression cassettes for transgenes of interest and, optionally, a selectable marker.

The phrase "expression cassette," also called a "transgene," is intended to include endogenous DNA sequences, which are found in the yeast strain being transformed, exogenous DNA sequences, which are not found in the yeast strain being transformed, as well as heterogeneous DNA sequences, which combine endogenous and exogenous DNA sequences. The expression cassette can include flanking elements necessary for gene expression, including a promoter and/or a terminator. In order to ensure good expression in the yeast, the promoters or terminators can be selected from sequences originating from the yeast. Promoters that can be used include promoters derived from genes involved in glycolysis, such as: the promoter of the PGK gene (encoding 3-phosphoglycerate kinase), the promoter of the GAPDH (TDH3) gene (encoding glyceraldehyde-3-phosphate dehydrogenase), the promoter of the ADH1 gene (encoding alcohol dehydrogenase 1), the promoter of the ENO1 gene (encoding enolase 1), or the promoter of the TPI1 gene (encoding triose phosphate isomerase).

Inducible promoters can also be used, including: a promoter of one of the galactose-regulated GAL genes or the GAL10/CYC1 hybrid promoter, the promoter of the CYC1 gene (encoding iso-1-cytochrome c, a mitochondrial electron transporter), which is regulated with oxygen and repressed by glucose, the methionine-repressible promoter of the MET25 gene (encoding O-acetylhomoserine (thio) lyase), the methionine-inducible promoter of the MET3 gene (encoding ATP sulphurylase), the copper-inducible promoter of the CUP1 gene (encoding copper chelatin), and the promoters of the CTR1 and CTR3 genes (encoding membrane copper transporters) which are repressed by copper at high concentration and induced by copper at low concentration.

The promoter of the TEF1 gene (encoding a transcription elongation factor), and the promoter of the PMA1 gene (encoding a membrane proton transporter ATPase) can also be used.

Terminators that can be used include NCP1, PGK, ADH1, as well as other endogenous yeast terminators.

The term "marker" is intended to mean any selectable marker that can be used in yeast, for example auxotrophic markers such as URA3, ADE2, HIS3, LEU2, TRP1 or LYS2, and resistance markers, such as natMX, for resistance to nourseothricin, the hphMX gene for resistance to hygromycin, or the KanMX gene for resistance to geneticin (G418).

Such markers can be present on the plasmids in order to ensure successful transformation of the strain by said plasmid. Auxotrophic markers allow selection for expression of the selectable marker gene, making it possible to eliminate yeast that lose this plasmid.

The term "origin of replication" is intended to mean a sequence which allows the plasmid to be recognized and replicated by the yeast although it is present in the yeast in circular form. A 2μ-type origin of replication originating from yeast extrachromosomal endogenous circular plasmids or the ARS CEN origin of replication, composed of one of the chromosomal ARS origin of replication sequences and of one of the CEN centromeric sequences, can be used in the yeast.

An expression cassette can be introduced into the yeast either via an integration plasmid or via an autonomous replicative plasmid.

The term "integration plasmid" is intended to mean the use of DNA sequences preferably comprising a selectable marker and at least one expression cassette for a gene(s) of interest. Integration plasmids are linearized before they are transformed into yeast, allowing their sequences to be inserted into regions of the *Saccharomyces cerevisiae* genome.

The term "autonomous replicative plasmid" is intended to mean an expression system comprising: a 2μ yeast origin of replication, one or two selectable markers, and at least one expression cassette for a gene(s) of interest. After transformation into yeast, this type of vector remains extrachromosomal in the form of a double-stranded circular DNA, replicating autonomously in the nucleus of the yeast (in other words, it does not integrate into the yeast's genome).

The process according to the present invention is based on the simultaneous transformation of a yeast strain with at least two different integration plasmids. It is therefore referred to as a "cotransformation." This process has the advantage of being simple and rapid since the multicopy integration is carried out in a single step.

The term "multicopy integration" is intended to mean the integration of at least two copies of the same sequence. The number of copies which integrate when the process according to the invention is carried out can vary from 2 to 20, preferably from 5 to 20, even more preferably from 8 to 12.

The second step of the process according to the invention consists of the selection of the best transformants, namely those which express the molecules of interest at the best titre. It is carried out in two stages.

In the first stage of the selection process, the strains having integrated the transgenes into their genome are selected, either through detection of the presence of the expression cassettes, or by phenotypic observation of the selectable marker when such a marker is present. A sufficient number of transformants is selected. A sufficient number is at least to 30 clones; in one embodiment, at least 40 clones are selected; in another embodiment, at least 50 clones are selected. This is because it has been demonstrated that the level of productivity is very heterogeneous in the population of transformants obtained by means of the process according to the invention. Consequently, in order allow selection of high-producing clones, it is necessary to start from quite a large population. Selecting only about ten clones, or less, as is conventionally done, does not optimize selection of the best producers. This aspect is demonstrated in the Examples.

In the second stage of the selection process, the best producing strains are selected using a test that will generally be a functional test.

This functional test is typically based on the productivity of the strains and the purity of the molecule of interest produced. Indeed, these two criteria are indissociable when seeking to select a strain having the properties necessary for its industrialization.

The term "productivity of the strain" is intended to mean its capacity for producing large amounts of a molecule(s) of interest.

The term "purity of the molecule of interest produced" is intended to mean the proportion of molecule of interest produced relative to intermediates or impurities associated with its production as by-products. The molecule of interest must be able to be separated from these products.

Such a functional test may be carried out according to the techniques known to those skilled in the art. To quantify production of a molecule of interest, of the yeast transformants can be screened using an appropriate assay, including Western blotting, ELISA assays, colorimetric tests, microbiological tests, liquid or gas chromatographies, etc. To quantify the production of an enzyme, the enzymatic activity in the culture medium can be assayed. The purity can typically be evaluated by means of chromatographic tests.

The best transformants obtained by means of the method according to the invention have a productivity which is greater by at least +30% compared with that of the best transformant obtained by means of the conventional method of transformation with an autonomous replicative plasmid. This gain in productivity is very significant from an industrial point of view, all the more advantageous since the quality in terms of purity is equivalent to that obtained with a conventional transformation.

The statistical analyses carried out on the populations of transformants have shown that the cotransformation of at least two integration plasmids is a relatively rare event. From a practical point of view, this means that it is necessary to screen a large population in order to identify the transformed strains having the highest levels of production, i.e. highest titres.

A molecular investigation has demonstrated that the integration takes place in multiple copies and that said integration is stable.

The process according to the invention therefore makes it possible to solve a frequently encountered problem, namely that it is difficult to obtain high producers. The solution consists of proposing a simple and rapid process allowing the stable integration of several transgenes in the same yeast.

The present process can be used to introduce genes which are endogenous or genes which are exogenous with respect to the yeast, depending on the desired objective.

Such applications include:
(i) the biosynthesis, by a yeast from a simple carbon source, such as glucose or ethanol, of enzymes which are part of a metabolic pathway, which is
either endogenous when said enzymes are limiting; by way of example, HMG1 and ERG1 for the production of sterols or sterol precursors,
or exogenous by combination of transgenes in order to generate a new metabolic pathway; by way of example, CYP71A1 for the production of artemisinic acid, or cytochrome P450 taxoid hydroxylases for the production of taxoids.

This system is also applicable to productions by bioconversion;
(ii) the direct production of recombinant proteins as molecule of interest; by way of example, any protein that it is desired to produce at a high level, such as invertase, etc., or proteins capable of interacting with one another, such as the heavy and light chains of immunoglobulins.

This method can be applied to various strains of yeasts, in particular *Saccharomyces cerevisiae* and *Pichia pastoris* and *Kluyveromyces lactis*.

In one preferred embodiment, the process previously described is applied to the production of steroids/hydrocortisone. To do this, the first plasmid comprises an expression cassette for the 3β-HSD and P450c11 enzymes, and the second plasmid comprises an expression cassette for the P450scc and ADX enzymes; the transformants having integrated the four transgenes are selected for their ability to produce steroids/hydrocortisone. The productivity is measured directly on the amount of hydrocortisone produced and the evaluation of the purity is based on the percentage of hydrocortisone relative to the total steroids.

The preparation of the hydrocortisone-producing strains is described in the examples which follow.

Another subject of the invention consists of the hydrocortisone-producing transformed strains directly obtained by means of the process according to the invention.

The present invention also relates to the use of the strains for producing hydrocortisone, and also to a method for producing hydrocortisone which consists in culturing the transformed strains according to the invention.

BRIEF DESCRIPTION OF THE FIGURES

FIG. 5: Principle of Southern blotting. A. Single-copy integration. B. Tandem multiple-copy integration. x: Signal corresponds to one copy. y: Signal characteristic of the inserted fragment corresponding to a multicopy integration, the strength of the signal being proportional to the number of copies inserted.

EXAMPLES

Figure 1:
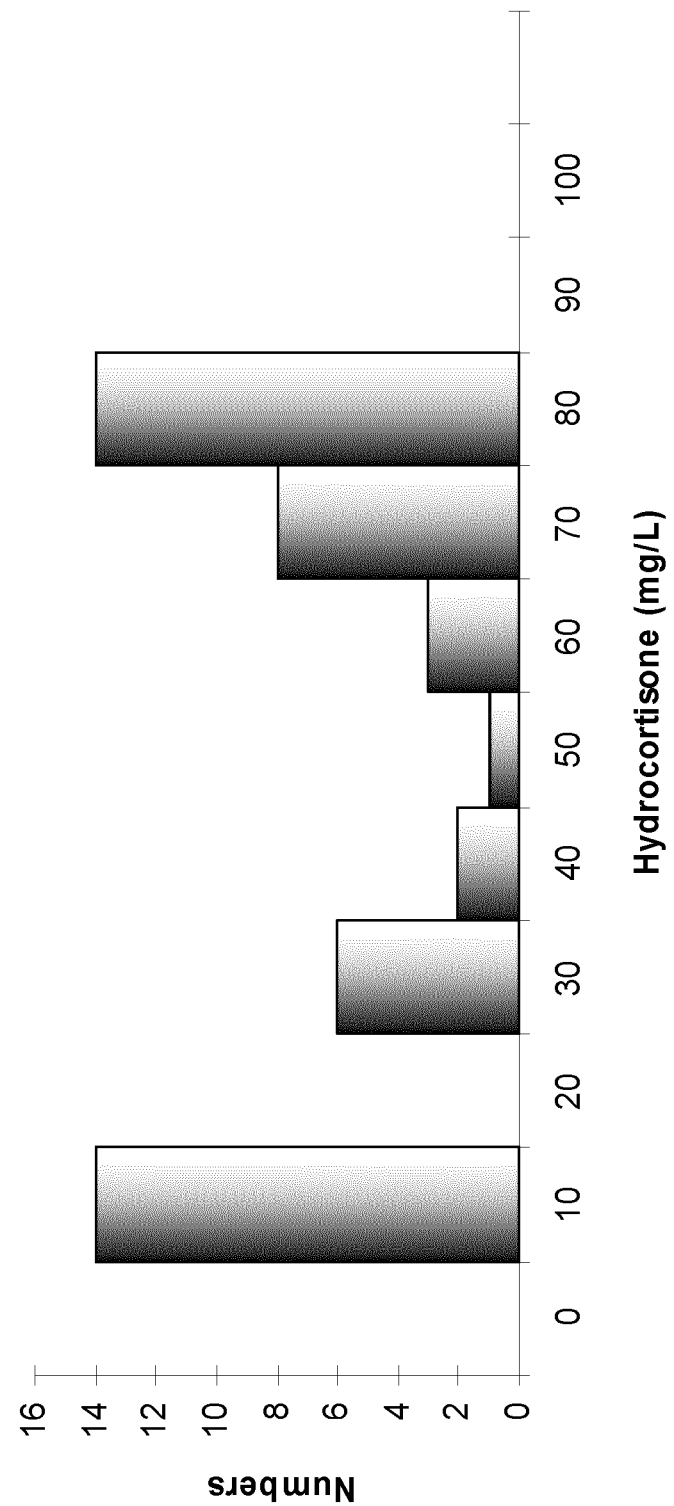
FIG. 1: Histogram of distribution of the BYM 16 strains transformed with the autonomous replicative plasmid pFM10.

Example 1: Obtaining Genetically Modified Yeasts Capable of Producing Hydrocortisone after Transformation with an Autonomous Replicative Plasmid a—Description of the Autonomous Replicative Plasmid The pFM10 plasmid has four expression cassettes and two "auxotrophic" selectable markers: an expression cassette for the P450scc heterologous gene of bovine origin (CYP11A1) in its mature form, i.e. with no mitochondrial targeting sequence; an expression cassette for the ADX heterologous gene of bovine origin in its mature form; an "auxotrophic" selectable marker URA3; an expression cassette for the 3βHSD heterologous gene of bovine origin; an expression cassette for the P450c11 chimeric heterologous gene (CYP11B1); and an "auxotrophic" selectable marker ADE2. The pFM10 plasmid also contains two short sequences, R1 and R2, of *Arabidopsis thaliana* (SEQ ID No. 1 and SEQ ID No. 2, respectively).

b—Transformation of the Plasmid

Plasmid preparation: The pFM10 plasmid, which lacks an origin of replication for *E. coli*, was prepared by amplification in the *S. cerevisiae* strain w303. The plasmid was extracted and purified from the w303 pFM10 strain which had been pretreated to obtain spheroplasts, using methods well known by those skilled in the art for manipulation of *S. cerevisiae*, as described by Becker and Lundblad (2001).

A PCR amplification with oligonucleotides specific for the 3βHSD heterologous gene (SEQ ID No. 3 and SEQ ID No. 4) was used to verify the efficiency and the quality of this extraction.

Transformation: The BYM16 strain, which is auxotrophic for adenine and uracil, was transformed with the pFM10 circular plasmid by means of a conventional method for transforming *S. cerevisiae* which results in a good transformation efficiency.

c—Selection of the Transformed Strains

Primary Screen:

This direct selection screen consists in selecting the transformed strains on a selective medium, i.e. a medium which lacks the components for which the yeast is auxotrophic. It is necessary to have a significant number of at least 30 transformants in order to carry out the secondary screen.

It consists in amplifying the 3βHSD heterologous gene by PCR with specific oligonucleotides (SEQ ID No. 3 and SEQ ID No. 4) that is to say using radiography with a probe specific for the 3βHSD gene (SEQ ID No. 8). This screen requires having a significant number of at least 500 to 1000 transformed strains selected on minimum medium supplemented with adenine.

"Functional" Secondary Screen:

After a step of growth on selective medium, the transformed strains were evaluated for their level of hydrocortisone production on the scale of an Erlenmeyer flask in "Käppeli" medium, which contains glucose and ethanol as carbon sources. After 3 days of incubation at 30° C. with shaking, 2% ethanol was added. The incubation was continued up to 7 days.

50 transformed strains were evaluated in order to carry out a statistical study of the level of hydrocortisone production, and to allow selection of the best producers according to their level of hydrocortisone production and percentage of hydrocortisone relative to total steroids.

At the end of production, the concentration of hydrocortisone and of intermediate steroids was measured by means of a suitable HPLC method.

The best candidates were selected based on the criteria of (1) high hydrocortisone productivity, and (2) a low level of steroid impurities, which are characteristics required for industrial exploitation of the strain from a regulatory point of view.

d—Result of the Functional Characterization of the Strains Obtained by Means of the Process According to Example 1

The pFM10 autonomous replicative plasmid was extracted from the w303 pFM10 strain.

The BYM16 strain was transformed using this preparation. The transformed strains were selected by applying the primary screen, and 50 of these strains were evaluated for their level of hydrocortisone production by applying the secondary screen.

The results are presented in FIG. 1. The average hydrocortisone titre observed was 43 mg/l for a dispersion of 142%.

The best producer strain exhibited a production of 79 mg/l and a percentage of hydrocortisone of 89%, meeting the criteria of an industrializable strain, namely a high productivity and a low level of steroid impurities.

Example 2: Obtaining Genetically Modified Yeasts Capable of Producing Hydrocortisone after Transformation with Integration Plasmids a—Description of the Integration Plasmids Two integration plasmids can be simultaneously introduced into the genome of *S. cerevisiae*, each making it possible to express at least two heterologous genes.

In the present invention, the plasmids used were:

The pFM7 plasmid, the pCB12 plasmid and the pBXL1505 plasmid.

The pFM7 plasmid has an expression cassette for the P450scc heterologous gene of bovine origin (CYP11A1) in its mature form, an expression cassette for the ADX heterologous gene of bovine origin in its mature form, and also an auxotrophic selectable marker URA3 (Duport et al., 1998).

The pCB12 plasmid has an expression cassette for the 3βHSD heterologous gene of bovine origin, an expression cassette for the P450c11 chimeric heterologous gene (CYP11B1), and also an auxotrophic selectable marker ADE2 (Dumas et al., 1996).

The pBXL1505 plasmid is derived from the pCB12 plasmid; the ADE2 selectable marker has been truncated so as to inactivate it.

Either of the pCB12 and pBXL1505 plasmids can be used without distinction.

b—Cotransformation of the Pplasmids

Plasmid Preparation:

The pFM7, pCB12 and pBXL1505 plasmids, which have an origin of replication for *E. coli*, were prepared by amplification in *E. coli* and extraction/purification, according to the usual methods implemented by those skilled in the art (Sambrook et al., 1989).

The pFM7 plasmid was cleaved by an Aat II restriction enzyme so as to linearise it. A single double-stranded linear DNA fragment of 10.5 kb comprising an expression cassette for the P450scc heterologous gene of bovine origin (CYP11A1) in its mature form, an expression cassette for the ADX heterologous gene of bovine origin in its mature form, and also a URA3 selectable marker and two sequences R1 and R2 (Duport et al., 1998) was thus obtained.

The pCB12 plasmid was cleaved by a BamHl restriction enzyme. Two double-stranded linear DNA fragments were obtained:
- a fragment of 2.7 kb,
- a 9.3 kb fragment of interest, containing an expression cassette for the 3βHSD heterologous gene of bovine origin, an expression cassette for the P450c11 chimeric heterologous gene (CYP11B1), an ADE2 selectable marker, and also two sequences R1 and R2 (Dumas et al., 1996).

The DNA fragment of 9.3 kb was purified according to conventional molecular biology techniques after isolation of the enzymatic restriction product by agarose gel electrophoresis.

In one experiment, the pBXL1505 plasmid was used instead of the pCB12 plasmid. The restriction enzyme treatment was identical, and the following fragments were obtained:
- a fragment of 2.7 kb,
- an 8.1 kb fragment of interest, comprising an expression cassette for the 3βHSD heterologous gene of bovine origin, an expression cassette for the P450c11 chimeric heterologous gene (CYP11B1), a truncated sequence of the ADE2 marker, and also two sequences R1 and R2.

Transformation:

In a first set of experiments, a strain exhibiting double auxotrophy for adenine and uracil was co-transformed with the following DNAs:
the linear DNA fragment of 10.5 kb of the pFM7 plasmid, and
the linear DNA fragment of 9.3 kb derived from the pCB12 plasmid.

In this case, the strain was rendered prototrophic.

In a second set of experiments, a strain exhibiting double auxotrophy for adenine and uracil was co-transformed with the following DNAs:
the linear DNA fragment of 10.5 kb of the pFM7 plasmid, and
the linear fragment of 8.1 kb derived from the pBXL1505 plasmid.

In this case, the strain remained auxotrophic for adenine. This cotransformation method makes it possible to simultaneously introduce four expression cassettes.

c—Selection of the Transformed Strains

The selection of the strains producing the highest hydrocortisone titres was carried out as described in Example 1, c.

For primaru screen, in the particular case of the cotransformation with a linear DNA fragment derived from the pBXL1505 plasmid and a linear DNA fragment of the pFM7 plasmid, this selection step consists in selecting the strains on a selective medium supplemented with adenine and free of uracil, and requires an additional screen in order to select the integration of the pBXL1505 linear fragment. I d—Results of the Functional Characterization of the Strains Cotransformation of the BYM16 Strain with the pFM7 and pCB12 Integration Plasmids:

36 strains co-transformed with linearized pFM7 plasmid and the 9.3 kb fragment of the pCB12 plasmid were selected by applying the primary screen, and these 36 strains were evaluated for hydrocortisone production by applying the secondary screen.

Figure 2:
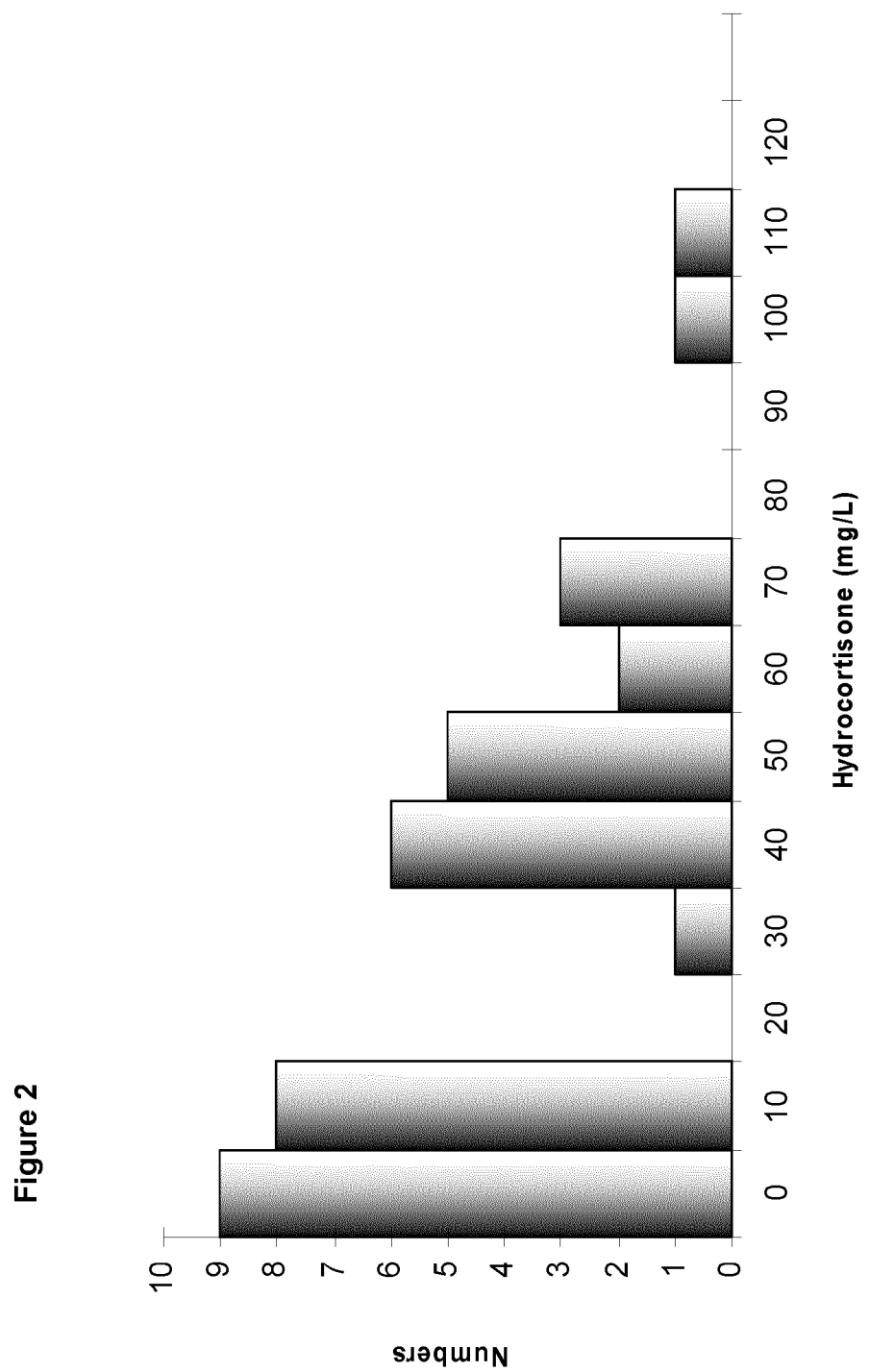
FIG. 2: Histogram of distribution of the BYM 16 strains transformed with the replicative integration plasmids pFM7 and pCB12.

The results are presented in FIG. 2. They show that the average hydrocortisone titre observed was 28 mg/l for a dispersion of 212%.

The best producer strain exhibited a production of 103 mg/l of hydrocortisone and a percentage of hydrocortisone of 85%, meeting the criteria of an industrializable strain, namely high productivity and low level of steroid impurities. It is called Strain A.

Cotransformation of the BYM16 Strain with the pFM7 and pBXL1505 Integration Plasmids 74 strains co-transformed with linearized pFM7 plasmid and the 8.1 kb fragment of the pBXL1505 plasmid were selected by applying the primary, and these 74 strains were evaluated for hydrocortisone production by applying the secondary screen.

Figure 3:
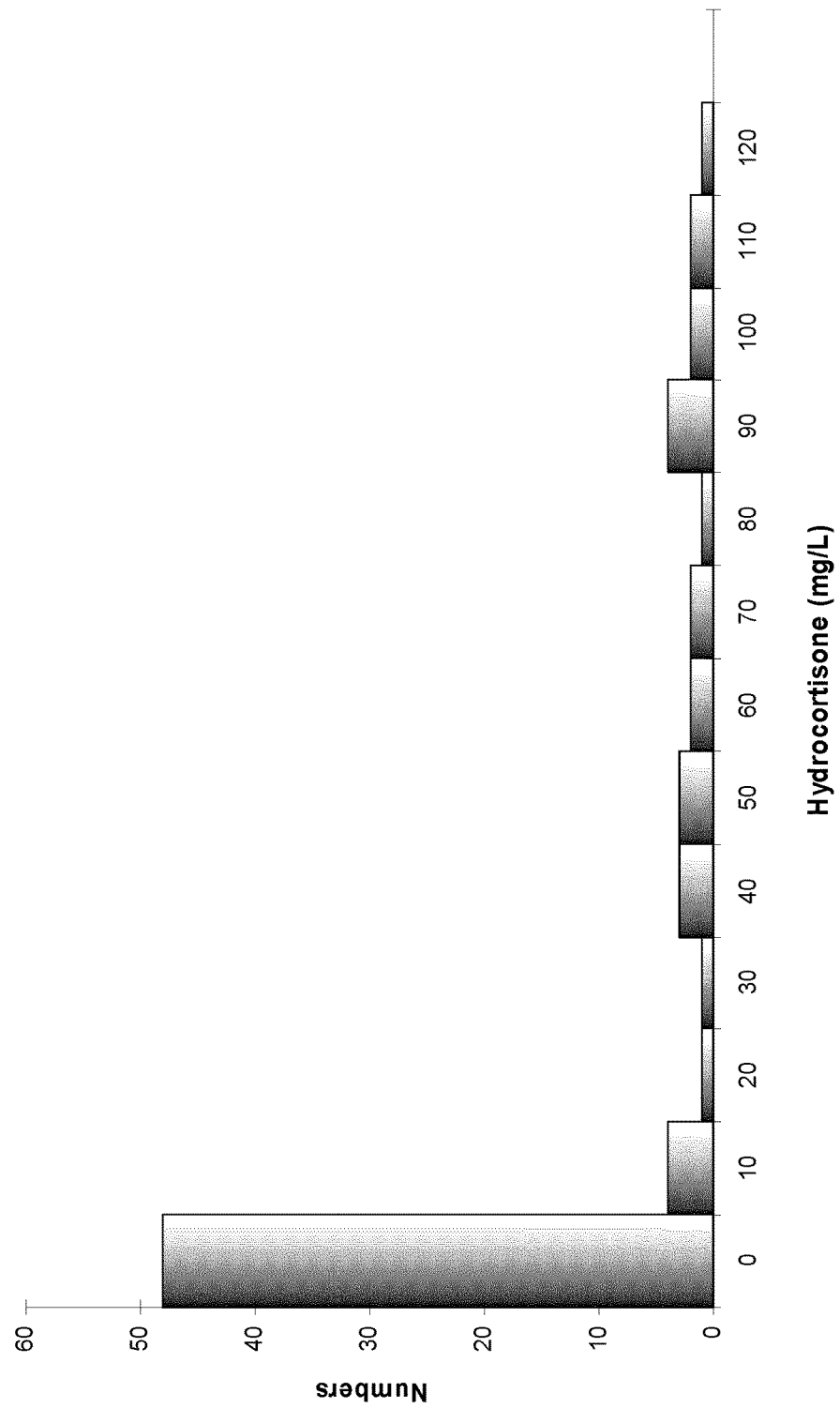
FIG. 3: Histogram of distribution of the BYM 16 strains transformed with the replicative integration plasmids pFM7 and pBXL1505.

The results are presented in FIG. 3. They show that the average hydrocortisone titre observed was 20 mg/l for a dispersion of 344%.

The best producer strain exhibited a production of 110 mg/l of hydrocortisone and a percentage of hydrocortisone of 85%, meeting the criteria of an industrializable strain, namely high productivity and low level of steroid impurities. It is called Strain B.

It was noted that the best producers obtained by means of the process according to the invention result from the combination of the plasmids as used in this example. These strains therefore comprise the best genetic combination among the combinations of plasmids tested.

Example 3: Comparison of the Transformed Strains

The best strains resulting from the cotransformations, Strain A and Strain B, cited in Example 2, d—, exhibited hydrocortisone production levels which were at least +30% higher compared with the best strain transformed with the pFM10 autonomous replicative plasmid, cited in Example 1.

Example 4: Molecular Investigations of the Strains Producing the Highest Hydrocortisone Titres In order to characterize the genotype of the best producer strains transformed with the pFM7 and pCB12 integration plasmids (Strain A) or the pFM7 and pBXL1505 integration plasmids (Strain B), two methods were applied:
1. Hybridization of chromosomes separated by pulsed-field electrophoresis,
2. Hybridization of genomic DNA fragments, termed Southern blotting technique.

1. Hybridization of Chromosomes Separated by Pulsed-Field Electrophoresis

It is possible to verify the integration of a gene, and also to localize it, by means of a hybridization on whole chromosomes. This involves separating the chromosomes using the "CHEF" (Contour Clamped Homogenous Electric Fields) technique, followed by specific hybridization for the integrated expression cassettes (Maule 1994).

To analyze Strain A and Strain B, a probe specific for the P450scc expression cassette (SEQ ID No. 7) of the pFM7 integration plasmid and a probe specific for the 3βHSD expression cassette (SEQ ID No. 8) of the pCB12 or pBXL1505 integration plasmids were constructed by PCR amplification and then radiolabelled with dCTP-$\alpha$-$^{32}$P.

Figure 4:
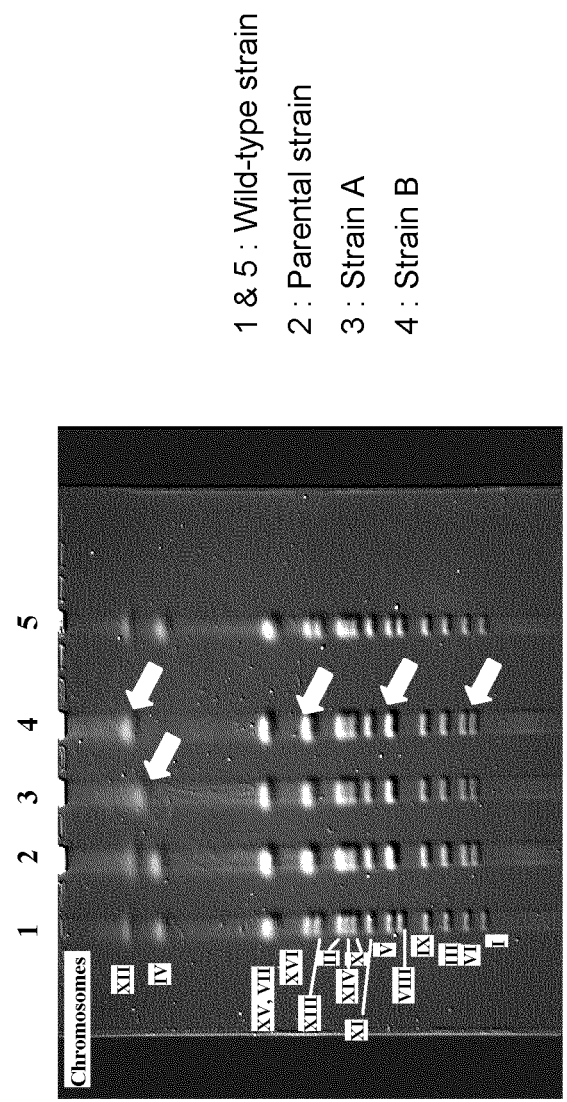
FIG. 4: Chromosomal profiles of the parental strain (lane 2) and of two prototypes producing hydrocortisone (lanes 3 and 4), compared with the wild-type strain (lanes 1 and 5).

This technique revealed that the DNA fragment containing the P450scc expression cassette and also the DNA fragment containing the 3βHSD expression cassette were located on chromosomes XII or IV (comigration) in strains A (FIG. 4, lane 3) and B (FIG. 4, lane 4). These strains show a single band in the region of chromosomes IV and XII. In comparison, the non-hydrocortisone-producing strains, namely the wild-type strain (FIG. 4, lanes 1 and 5) and the parental strain (FIG. 4, lane 2), show a migration profile with two bands. These differential characteristics therefore make it possible to establish a specific genetic fingerprint common to the strains according to the invention which are capable of producing hydrocortisone.

2. Hybridization by Southern Blotting

Southern blotting makes it possible to pinpoint the presence of an endogenous or exogenous DNA sequence in genomic DNA partially cleaved with "restriction" enzymes. This pinpointing is done by hybridization of this sequence with a labelled specific probe (Southern, 1975).

Depending on the type of enzymatic restriction applied to the genomic DNA, it is possible to reveal the manner in which this sequence is integrated: single integration, multiple integration in various regions or loci of the genome, or multiple tandem integration in a single locus (FIG. 5).

In order to characterize the overproducing strains, a probe specific for the P450scc expression cassette (SEQ ID No. 7) and a probe specific for the 3βHSD expression cassette (SEQ ID No. 8) were used. The genomic DNAs extracted from these strains was cleaved either with HpaI in order to reveal the presence of the 3βHISD expression cassette, or with EcoRV in order to reveal the presence of the P450scc expression cassette (see FIG. 5).

This technique revealed that the DNA fragment containing the P450scc expression cassette and also the DNA fragment containing the 3βHSD expression cassette were integrated in a tandem of at least ten copies.

These integration profiles were observed in several descendents of the best producers and proved to be identical. These integrations are therefore genetically stable.

These random multiple integrations therefore confer both strain stability and a gain in function in terms of hydrocortisone production.

DESCRIPTION OF THE BIOLOGICAL MATERIAL USED

List of the Plasmids Described in the Present Application

[pFM7: ori E. coli ori 2μ yeast R1 $P_{Gal10/CYC1}$-matADXbov-$T_{PGK1}$ URA3 $P_{Gal10/CYC1}$-P450sccbov-$T_{PGI1}$ R2]

[pCB12: ori E. coli R2 $P_{CYC1}$-P450c11hybrid-$T_{PGK1}$ ADE2 $P_{TDH3}$-3βHSDbov-$T_{PGK1}$ R1]

[pBXL1505: ori E. coli R1 $P_{TDH3}$-3βHSDbov-$T_{PGK1}$ ade2 $P_{CYC1}$-P450c11hybrid-$T_{PGK1}$ R2]

[pFM10: ori 2μ yeast R1 $P_{Gal10/CYC1}$-matADXbov-$T_{PGK1}$ URA3 $P_{Gal10/CYC1}$-P450sccbov-$T_{PGK1}$ R2 $P_{CYC1}$-P450c11hybrid-$T_{PGK1}$ ADE2 $P_{TDH3}$-3βHSDbov-$T_{PGK1}$]

List of the Strains Described in the Present Application

BYM16
Genotype
MATa, ura3-52, LEU2::$P_{CYC1}$-ARH1-$T_{PGK1}$, TRP1::$P_{TDH3}$-c17bov-$T_{NCP1}$_$P_{TEF1}$-ADRbov-$T_{PGK1}$
ypr1::$P_{TEF1}$-(c21human)n-$T_{PGK1}$, gyc1::$P_{TDH3}$-c21human-$T_{PGK1}$, atf2::$P_{TEF1}$-KanMX-$T_{TEF1}$,
ade2::$P_{GAL10/CYC1}$-sterol Δ7REDArabidopsis-$T_{PGK1}$, HIS3::$P_{TEF1}$-c17bov-$T_{PGK1}$_$P_{TDH3}$-COXVI yeast ADXbov-$T_{NCP1}$, gal80
Phenotype
a-mater Leu+ His+ Trp+ Ura− Ade− G418R
BYM16 Transformed with the pCB12 and pFM7 Integration Plasmids Genotype
MATa, ura3-52, LEU2::$P_{CYC1}$-ARH1-$T_{PGK1}$, TRP1::$P_{TDH3}$-c17bov-$T_{NCP1}$_$P_{TEF1}$-ADRbov-$T_{PGK1}$
ypr1::$P_{TEF1}$-(c21human)n-$T_{PGK1}$, gyc1::$P_{TDH3}$-c21human-$T_{PGK1}$, atf2::$P_{TEF1}$-KanMX-$T_{TEF1}$,
ade2::$P_{GAL10/CYC1}$-sterol Δ7REDArabidopsis-$T_{PGK1}$, HIS3::$P_{TEF1}$-c17bov-$T_{PGK1}$_$P_{TDH3}$-COXVI yeast ADXbov-$T_{NCP1}$, gal80
Random integration in multiple copies of: ($P_{GAL10/CYC1}$-ADX-$T_{PGK1}$)n, ($P_{GAL10/CYC1}$-P450scc-$T_{PGK1}$)n, ($P_{TDH3}$-3βHSD-$T_{NCP1}$)n, ($P_{CYC1}$-P450c11hybrid-$T_{PGK1}$)n, URA3n, ADE2n
Phenotype
a-mater Leu+ His+ Trp+ Ura+ Ade+ G418R BYM16 Transformed with the pBXL1505 and pFM7 Integration Plasmids Genotype
MATa, ura3-52, LEU2::$P_{CYC1}$-ARH1-$T_{PGK1}$, TRP1::$P_{TDH3}$-c17bov-$T_{NCP1}$_$P_{TEF1}$-ADRbov-$T_{PGK1}$
ypr1::$P_{TEF1}$-(c21human)n-$T_{PGK1}$, gyc1::$P_{TDH3}$-c21human-$T_{PGK1}$, atf2::$P_{TEF1}$-KanMX-$T_{TEF1}$,
ade2::$P_{GAL10/CYC1}$-sterol Δ7REDArabidopsis-$T_{PGK1}$, HIS3::$P_{TEF1}$-c17bov-$T_{PGK1}$_$P_{TDH3}$-COXVI yeast ADXbov-$T_{NCP1}$, gal80
Random integration in multiple copies of: ($P_{GAL10/CYC1}$-ADX-$T_{PGK1}$)n, ($P_{GAL10/CYC1}$-P450scc-$T_{PGK1}$)n, ($P_{TDH3}$-3βHSD-$T_{NCP1}$)n, ($P_{CYC1}$-P450c11hybrid-$T_{PGK1}$)n, URA3n, ADE2n
Phenotype
a-mater Leu+ His+ Trp+ Ura+ Ade− G418R BYM16 Transformed with the pFM10 Autonomous Replicative Plasmid Genotype
MATa, ura3-52, LEU2::$P_{CYC1}$-ARH1-$T_{PGK1}$, TRP1::$P_{TDH3}$-c17bov-$T_{NCP1}$_$P_{TEF1}$-ADRbov-$T_{PGK1}$
ypr1::$P_{TEF1}$-(c21human)n-$T_{PGK1}$, gyc1::$P_{TDH3}$-c21human-$T_{PGK1}$, atf2::$P_{TEF1}$-KanMX-$T_{TEF1}$,
ade2::$P_{GAL10/CYC1}$-sterol Δ7REDArabidopsis-$T_{PGK1}$, HIS3::$P_{TEF1}$-c17bov-$T_{PGK1}$_$P_{TDH3}$-COXVI yeast ADXbov-$T_{NCP1}$, gal80
[pFM10: 2μ-URA3-ADE2 $P_{GAL10/CYC1}$-ADX-$T_{PGK1}$ $P_{GAL10/CYC1}$-P450scc-$T_{PGK1}$ $P_{TDH3}$-3βHSD-$T_{NCP1}$ $P_{CYC1}$-P450c11hybrid-$T_{PGK1}$]
Phenotype
a-mater Leu+ His+ Trp+ Ura+ Ade+ G418R W303 pFM10
Genotype
MATa leu2-3, 112 trp1-1, can1-100, ura3-1, ade2-1, his3-11,15[phi$^+$]
[pFM10: 2μ-URA3-ADE2 $P_{GAL10/CYC1}$-ADX-$T_{PGK1}$ $P_{GAL10/CYC1}$-P450scc-$T_{PGK1}$ $P_{TDH3}$-3βHSD-$T_{NCP1}$ $P_{CYC1}$-P450c11hybrid-$T_{PGK1}$]
Phenotype
a-mater Leu− His− Trp− Ura+ Ade+

LITERATURE REFERENCES

Becker D. and Lundblad V. (2001). Manipulation of yeast genes. Introduction of DNA into yeast cells. *Curr. Protoc. Mol. Biol.*, Chapter 13-Unit 13.7:1-10.

Broach J. R. (1983). Construction of high copy vectors using 2 μm circle sequences. *Method Enzymol.* 101: 307-325.

Brocard-Masson C. and Dumas B. (2006). The fascinating world of steroids: S. cerevisiae as a model organism for the study of hydrocortisone biosynthesis. *Biotechnol. Genet. Eng. Rev.*, 22:213-52

Dumas B., Cauet G., Lacour T., Degryse E., Laruelle L., Ledoux C., Spagnoli R., and Achstetter T. (1996). 11 beta-hydroxylase activity in recombinant yeast mitochondria. In vivo conversion of 11-deoxycortisol to hydrocortisone. *Eur J Biochem.* 238:495-504.

Dumas B., Brocard-Masson C., Assemat-Lebrun K., Achstetter T. (2006). Hydrocortisone made in yeast: Metabolic engineering turns a unicellular microorganism into a drug-synthesizing factory. *Biotechnol.*, 1:299-307.

Duport C., Spagnoli R., Degryse E., and Pompon D. (1998). Self-sufficient biosynthesis of pregnenolone and progesterone in engineered yeast. *Nat Biotechnol.* 16:186-9.

Ito H, Fukuda Y, Murata K, Kimura A. (1983).Transformation of intact yeast cells treated with alkali cations. J. Bacteriol., 153: 163-168.

Klebe R. J., Harriss J. V., Sharp Z. D., Douglas M. G. (1983). A general method for polyethylene-glycol-induced genetic transformation of bacteria and yeast. Gene, 25(2-3): 333-41.

Lopes T. S., Klootwijk J., Veenstra A. E., Van der Aar P. C., Van Heerikhuizen H., Raué H. A., Planta, R. J. (1989). High-copy-number integration into the ribosomal DNA of *Saccharomyces cerevisiae*: a new vector for high-level expression. Gene 79 199-206.

Lopes T. S., Hakkaart G.-J. A. J., Koerts B. L., Raué H. A., Planta R. J. (1991). Mechanism of high-copy-number integration of pMIRY-type vectors into the ribosomal DNA of *Saccharomyces cerevisiae*. Gene, 105 83-90.

Maule J. (1994). Electrophoretic Karyotype Analysis, PFGE, pages 221-252, in "Methods, vol. 29: Chromosome Analysis Protocole", edited by: J. R. Gosden, Humana Press Inc., Totowa, N.J.

Ménard Szczebara F., Chandelier C., Villeret C., Masurel A., Bourot S., Duport C., Blanchard S., Groisillier A., Testet E., Costaglioli P., Cauet G., Degryse E., Balbuena D., Winter J., Achstetter T., Spagnoli R., Pompon D., Dumas B. (2003). Total biosynthesis of hydrocortisone from a simple carbon source in yeast. Nature biotechnology, 21(2): 143-149.

Sambrook J., Fritsch E. F. and Maniatis T. Molecular cloning, 2nd edition. (1989). Cold Spring Harbor Laboratory Press.

Southern, E. M. (1975). Detection of specific sequences among DNA fragments separated by gel electrophoresis. *J. Mol. Biol.* 98: 503-517.

All references cited above are hereby incorporated by reference.

The invention claimed is:

1. A method for producing hydrocortisone from yeast to achieve production of at least 100 mg/L hydrocortisone, the method comprising:
    (a) providing two integration plasmids, each integration plasmid comprising at least two expression cassettes, such that the two integration plasmids together comprise at least four expression cassettes, wherein the four expression cassettes of the two integration plasmids are P450scc, adrenodoxin (ADX), P450c11, and 3β-hydroxysteroid dehydrogenase (3β-HSD);
    (b) stably integrating multiple copies of the two integration plasmids into a population of yeast cells, by co-transforming the plasmids into the yeast;
    (c) performing a primary screen of 500 to 1000 transformed yeast clones, wherein selection of the yeast clones is based on the presence of the expression cassettes, or selection for the expression of a selectable marker when such a marker is present;
    (d) performing a functional secondary screen on at least 30 yeast clones selected in the primary screen to identify a yeast isolate producing at least 100 mg/L hydrocortisone, wherein the yeast isolate comprises multiple copies of each of the integration plasmids and the multiple copies of the integration plasmids are stably integrated into the chromosomes of the yeast isolate;

(e) culturing the yeast isolate in a culture medium; and (f) recovering and purifying said hydrocortisone from the culture medium.

2. The method of claim 1, wherein from 5 to 20 copies of the plasmids are stably integrated into the chromosomes of the yeast isolate.

3. The method of claim 1, wherein from 8 to 12 copies of the plasmids are stably integrated into the chromosomes of the yeast isolate.

4. The method of claim 1, wherein at least 40 clones are selected by the primary screen.

5. The method of claim 2, wherein the yeast is *Saccharomyces cerevisiae*.

6. The method of claim 1, wherein at least one of the plasmids comprises an auxotrophic selectable marker.

7. The method of claim 6, wherein the auxotrophic marker is selected from the group consisting of ADE2, URA3, HIS3, LEU2, TRP1, and LYS2.

8. The method of claim 1, wherein at least one of the plasmids comprises a selectable marker which is a resistance marker.

9. The method of claim 8, wherein the resistance marker is selected from the group consisting of natMX, phMX, and KanMX.

10. The method of claim 7, wherein one of the plasmids comprises URA3 and the other plasmid comprises ADE2.

11. The method of claim 1, wherein at least 85% of the steroid produced by the yeast is hydrocortisone.

12. The method of claim 1, wherein each integration plasmid further comprises a selectable marker.

* * * * *